US007253139B2

United States Patent
Behler et al.

(10) Patent No.: US 7,253,139 B2
(45) Date of Patent: Aug. 7, 2007

(54) SURFACTANT PREPARATIONS COMPRISING α-HYDROXY ACIDS

(75) Inventors: Ansgar Behler, Bottrop (DE); Werner Seipel, Hilden (DE); Heike Kublik, Kempen (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 132 days.

(21) Appl. No.: 10/479,337

(22) PCT Filed: May 22, 2002

(86) PCT No.: PCT/EP02/05587

§ 371 (c)(1),
(2), (4) Date: Jun. 25, 2004

(87) PCT Pub. No.: WO02/097022

PCT Pub. Date: Dec. 5, 2002

(65) Prior Publication Data

US 2004/0242444 A1  Dec. 2, 2004

(30) Foreign Application Priority Data

May 30, 2001 (DE) .................. 101 26 196

(51) Int. Cl.
*C11D 1/02* (2006.01)
*C11D 1/74* (2006.01)
*C11D 3/20* (2006.01)
*A61K 8/46* (2006.01)

(52) U.S. Cl. .............. 510/127; 510/414; 510/426; 510/434; 510/477; 510/492; 510/505; 424/401; 424/70.22

(58) Field of Classification Search ............ 510/127, 510/414, 426, 434, 477, 492, 505; 424/401, 424/70.22
See application file for complete search history.

(56) References Cited

U.S. PATENT DOCUMENTS

| 3,662,054 A |   | 5/1972 | Wollmann et al. |
| 3,962,150 A |   | 6/1976 | Viola |
| 6,190,675 B1 | * | 2/2001 | Beerse et al. ............ 424/401 |
| 6,710,082 B1 | * | 3/2004 | Pi Subirana et al. ...... 514/553 |

FOREIGN PATENT DOCUMENTS

| CA | 1 087 955 |   | 10/1980 |
| DE | 196 22 214 |   | 12/1997 |
| DE | 19622214 | * | 12/1997 |
| WO | WO 97/25965 | * | 7/1997 |
| WO | WO 98/55093 | * | 12/1998 |
| WO | WO 01/60332 |   | 8/2001 |

OTHER PUBLICATIONS

Kaestner et al., Hautirritationen verschiedener anionaktiver Tenside im Duhring-Kammer-Test am Menschen im Vergleich zu in vitro und tierexperimentellen Methoden, Fette, Seifen, Anstrichmittel, vol. 83, 1981, pp. 33-46, not translated.

Koeszegi et al., "Der HET-CAM-Test," Euro Cosmetics, Nov. 12, 1999, pp. 29-33, not translated.

Klaus Kuenstler, "Alternative Methoden in der Industrie am Beispiel der Haut- und Schleimhautvertraeglichkeitspruefung," Schuppan/Hardegg, Tierschutz durch Alternativen, Gustav Fischer Verlag, Stuttgart, 1988, pp. 67-69, 73-85, not translated.

* cited by examiner

*Primary Examiner*—Brian Mruk
(74) *Attorney, Agent, or Firm*—John F. Daniels; Daniel S. Ortiz

(57) ABSTRACT

A process for enhancing skin, mucous membranes and textile compatibility with an anionic surfactant composition involving: (a) providing an anionic surfactant composition; (b) providing an acid selected from the group consisting of a hydroxycarboxylic acid, a salt of a hydroxycarboxylic acid, an ester of a hydroxycarboxylic acid with an ethoxylated alcohol, and mixtures thereof; and (c) mixing (a) and (b).

13 Claims, No Drawings

SURFACTANT PREPARATIONS COMPRISING α-HYDROXY ACIDS

BACKGROUND OF THE INVENTION

This application is a 371 of PCT/EP02/05587 filed May 22, 2002.

This invention relates to surfactant preparations containing α-hydroxy acids which are distinguished by improved dermatological and mucous membrane compatibility and to the use of hydroxycarboxylic acids and/or salts and/or esters thereof with ethoxylated alcohols for reducing the irritation potential of surfactants.

In the development of new surfactants, practical consumer protection is the primary consideration. Time and again, surfactants with very good performance properties have been found not to meet the criteria of local compatibility. Anionic surfactants in particular are known to have a high irritation potential [Kästner, W. and Frosch, J. P., Hautirritationen verschiedener anionaktiver Tenside im Duhring-Kammer-Test am Menschen im Vergleich zu in vitro und tierexperimentellen Methoden in Fette, Seifen, Anstrichmittel 83, 1981, pages 33-46]. Local compatibility is said to be dependent upon the C chain length and the degree of ethoxylation. Chain lengths of 10 to 14 carbon atoms and surfactants with a low degree of ethoxylation show poor dermatological compatibility. Although this knowledge can be embraced in product development, a loss of favorable performance properties often has to be accepted.

Accordingly, there is still a need on the market even today—despite a large number of highly compatible surfactants—for substances which combine these properties with one another and, despite favorable detersive properties, compatibility with other auxiliaries and optimal processing behavior—also show very good dermatological compatibility.

Accordingly, the problem addressed by the present invention was to reduce the irritation potential of surfactants and to provide preparations containing anionic surfactants which would have high surface activity but which would still show improved compatibility with the skin, mucous membrane and textiles.

DESCRIPTION OF THE INVENTION

The present invention relates to the use of hydroxycarboxylic acids and/or salts and/or esters thereof with ethoxylated alcohols for improving the compatibility of anionic surfactants with the skin, mucous membrane and textiles, characterized in that hydroxycarboxylic acids and/or salts and/or esters thereof with ethoxylated alcohols are added to the surfactants or surfactant solutions.

The present invention also relates to preparations containing
(a) anionic surfactants and
(b1) 0.1 to 20% by weight α-hydroxycarboxylic acids and/or salts thereof and/or
(b2) 25 to 50% by weight of esters of α-hydroxycarboxylic acids with ethoxylated alcohols, based on the quantity of anionic surfactants, characterized in that they have a surface activity of at least 20 mN/m (as measured at room temperature by the Wilhelmy plate method (platinum plate T11 to DIN 53914) and in that they have a Q value in the HET-CAM test of less than 75%, based on the surfactant solution without α-hydroxycarboxylic acid.

It has surprisingly been found that the addition of hydroxycarboxylic acids and/or salts thereof and/or esters thereof with ethoxylated alcohols to anionic surfactants greatly reduces the irritation potential of the surfactants and hence considerably improves their compatibility with the skin, mucous membrane and textiles without any loss of detersive activity.

Preparations containing anionic surfactants in combination with 0.1 to 20% by weight of α-hydroxycarboxylic acids and/or salts and/or esters thereof with ethoxylated alcohols show considerably better compatibility than the pure surfactant formulations as reflected in the fact that the reaction time value in the HET-CAM test can be improved by at least 25%, based on the starting value of the pure surfactant formulation. This result had not be expected because, in antimicrobial detergents in particular, antimicrobial agents and anionic surfactants are combined with carboxylic acids to achieve better antimicrobial activity. The acid is said to reduce the negative charge of the bacterial cell walls and easily to overcome the cell membrane—weakened by the surfactant—in order to shift the pH in the cytoplasm of the cell (cf. International patent application WO 98/55093, page 10). This is a mechanism which, applied to the cells of human skin, certainly does not suggest high compatibility.

HET-CAM Test

The HET-CAM test (hen's egg test/chorioallantois membrane test) is a test for determining the acute mucous-membrane-irritating effect of substances on the vascular system of the chorioallantois membrane (CAM) of fertilized hens' eggs incubated for 10 days [Köszegi, Dunja et al.: Der HET-CAM-Test, Euro Cosmetics 11/12-99, pp. 29-33, Künstler, Klaus: Alternative Methoden in der Industrie am Beispiel der Haut-und Schleimhautverträglichkeitsprüfung in Schuppan/Hardegg, Tierschutz durch Alternativen, Gustav Fischer Verlag, Stuttgart 1988].

The chorioallantois membrane which develops during incubation contains an efficient vascular system. It is exposed by removing the egg shell above the air chamber and covered with 300 µl of the solution to be tested. The reactions of the vascular system to the substances are observed for up to 300 seconds. The degree of irritation is evaluated according to type and onset time. The reaction time is the time in seconds between application and appearance of the reaction parameter. Hemorrhage (bleeding), lysis (dissolving of the blood vessels) and coagulation (congealing of the egg white) are evaluated as reaction parameters. Through the reaction time, an irritation value [Q] is drawn up as a measure of the particular test substance by comparison with a reference substance (Texapon ASV, 5% active substance).

| Irritation value [Q] | Degree of irritation |
|---|---|
| 0.8 | Mildly irritating |
| $\leq 0.8 < 1.2$ | Moderately irritating |
| $\geq 1.2 < 2.0$ | Irritating |
| $\geq 2.0$ | Highly irritating |

According to the present invention, the addition of hydroxycarboxylic acids and/or salts and/or esters thereof with ethoxylated alcohols is intended considerably to reduce the irritation potential of anionic surfactants. After addition of the acid and/or salt and/or ester thereof with ethoxylated alcohols, the Q value of the surfactant preparation without hydroxycarboxylic acid is intended to be only 75% of the starting value. A reduction to 70% of the value of the hydroxycarboxylic-acid-free formulation is preferred and a reduction to 65% of that value is particularly preferred.

Determination of Surface Activity

Surface activity was determined to DIN 53914. To this end, the solution to be tested was tested by the Wilhelmy plate method (plate PT 11) at 21±1° C. The preparations according to the invention are intended to have a surface activity of at least 20 mN/m, preferably at least 25 mN/m and more particularly at least 30 mN/m, based on the active substance content of 5% by weight.

Anionic Surfactants

Typical examples of anionic surfactants of the preparations according to the invention are soaps, alkyl benzenesulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, the polyglycol ether chains may have a conventional homolog distribution, although they preferably have a narrow homolog distribution. However, preferred anionic surfactants in the preparations according to the invention are alkyl sulfates, fatty alcohol ether sulfates, alkane sulfonates and alkyl sulfosuccinates (among which the alkyl and/or alkenyl sulfates are particularly preferred) and the alkyl ether sulfates.

Alkyl and/or alkenyl sulfates, which are often also referred to as fatty alcohol sulfates, are understood to be the sulfation products of primary alcohols which correspond to formula (I):

in which $R^2$ is a linear or branched, aliphatic alkyl and/or alkenyl group containing 6 to 22 carbon atoms and preferably 12 to 18 carbon atoms and X is an alkali metal and/or alkaline earth metal, ammonium, alkyl ammonium, alkanolammonium or glucammonium. Typical examples of alkyl sulfates which may be used in accordance with the invention are the sulfation products of caproic alcohol, caprylic alcohol, capric alcohol, 2-ethyl hexyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by high-pressure hydrogenation of technical methyl ester fractions or aldehydes from Roelen's oxo synthesis. The sulfation products may advantageously be used in the form of their alkali metal salts and particularly their sodium salts. Alkyl sulfates based on $C_{16/18}$ tallow fatty alcohols or vegetable fatty alcohols of comparable C chain distribution in the form of their sodium salts are particularly preferred.

Alkyl ether sulfates ("ether sulfates") are known anionic surfactants which, on an industrial scale, are produced by $SO_3$ or chlorosulfonic acid (CSA) sulfation of fatty alcohol or oxoalcohol polyglycol ethers and subsequent neutralization. Ether sulfates suitable for use in accordance with the invention correspond to formula (II):

in which $R^1$ is a linear or branched alkyl and/or alkenyl radical containing 6 to 22 carbon atoms, m is a number of 0 or 1 to 10 and X is an alkali metal and/or alkaline earth metal, ammonium, alkylammonium, alkanol-ammonium or glucammonium. Typical examples are the sulfates of addition products of on average 1 to 10 and more particularly 2 to 5 mol ethylene oxide onto caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof in the form of their sodium and/or magnesium salts. The ether sulfates may have both a conventional homolog distribution and a narrow homolog distribution. It is particularly preferred to use ether sulfates based on adducts of on average 1.5 to 2.5 mol ethylene oxide with technical $C_{12/14}$ or $C_{12/18}$ coconut fatty alcohol fractions in the form of their sodium and/or magnesium salts.

The anionic surfactants are present in the preparations according to the invention in quantities of 1 to 99% by weight, preferably in quantities of 2 to 30% by weight and more particularly in quantities of 10 to 20% by weight, based on the quantity of active substance.

Accordingly, the present invention also relates to preparations containing (a) 2 to 30% by weight anionic surfactants and (b1) 0.1 to 20% by weight α-hydroxycarboxylic acids and/or salts thereof and/or (b2) 25 to 50% by weight of esters α-hydroxycarboxylic acids with ethoxylated alcohols, based on the quantity of anionic surfactants, characterized in that they have a surface activity of at least 20 mN/m (as measured at room temperature by the Wilhelmy plate method (platinum plate T11 to DIN 53914) and in that they have a Q value in the HET-CAM test of less than 75%, based on the surfactant solution without α-hydroxycarboxylic acid.

Hydroxycarboxylic Acids and Salts and Esters thereof with Ethoxylated Alcohols

Hydroxycarboxylic acids are organic acids which, besides at least one COOH group, contain at least one OH group in the molecule. With one OH group, they may be present as monohydroxycarboxylic acids, with two OH groups as dicarboxylic acids or, with more than two OH groups, as polyhydroxycarboxylic acids. Hydroxycarboxylic acids are referred to as α-, β- and γ-hydroxycarboxylic acids according to the position of the OH group to the COOH group. The acids may be saturated or unsaturated (example: ricinoleic acid). Known aromatic hydroxycarboxylic acids are salicylic acid (2-hydroxybenzoic acid) and gallic acid (3,4,5-trihydroxybenzoic acid).

According to the present invention, preferred hydroxycarboxylic acids are α-hydroxycarboxylic acids, more particularly tartaric acid, mandelic acid, lactic acid, malic acid, citric acid and salts thereof.

The preparations according to the invention contain 0.1 to 20% by weight, preferably 1 to 15% by weight and more particularly 5 to 10% by weight of α-hydroxycarboxylic acids and/or salts thereof, based on the quantity of anionic surfactants.

The esters of the hydroxycarboxylic acids with ethoxylated alcohols are known compounds which correspond to formula (III):

$$R^3\text{-}(EO)_x\text{-}Z \qquad (III)$$

in which $R^3$ is an alkyl group containing 6 to 22 carbon atoms and preferably 12 to 14 carbon atoms, X is an integer of 1 to 20 and preferably 2 to 10 and Z is a hydroxycarboxylic acid residue. According to the invention, preferred hydroxycarboxylic acids as the residue Z are hydroxycarboxylic acids, more particularly tartaric acid, mandelic acid, lactic acid, malic acid, citric acid.

The preparations according to the invention contain 25 to 50% by weight of esters of the hydroxycarboxylic acids with alkyl ethoxylates, based on the quantity of anionic surfactants.

Commercial Applications

The preparations according to the invention are intended to be used—but not exclusively—for the production of cosmetic preparations, dental care preparations, laundry detergents, dishwashing detergents and cleaners.

The preparations according to the invention containing anionic surfactants in combination with α-hydroxycarboxylic acids and/or salts and/or ester thereof with ethoxylated alcohols may contain any products through which the skin may come into contact with anionic surfactants in order to reduce the risk of irritation.

Depending on the particular application envisaged, the preparations according to the invention may contain other auxiliaries, but not antimicrobial agents. They may be present in solid form but are preferably present in the form of an aqueous or alcoholic/aqueous solution. The pH value of the preparations should be between pH 4 and pH 7 and is preferably between pH 5 and pH 6.8 and more particularly between pH 6 and pH 6.6.

For cosmetic and/or pharmaceutical applications, they may contain other mild surfactants, emulsifiers, lipid layer enhancers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

If the surfactant mixtures according to the invention are used for the production of detergents, the preparations may contain other typical ingredients such as, for example, solvents, hydrotropes, bleaching agents, bleach activators, detergency boosters, builders, viscosity adjusters, enzymes, enzyme stabilizers, optical brighteners, soil repellents, foam inhibitors, inorganic salts and perfumes and dyes.

EXAMPLES

Determination of Surface Tension

The surface tension of the surfactant solution containing tartaric acid was compared with that of the pure surfactant solution (Texapon® NSO, sodium lauryl ether sulfate; Cognis, Dusseldorf) by conducting measurements at 21±1° C. using the Wilhelmy plate method (plate PT 11) to DIN 53914.

TABLE 1A

Surface tension of the surfactant solution containing tartaric acid and the pure surfactant solution

| Substance | Concentration | Surface tension |
|---|---|---|
| Texapon ® NSO | 5% by weight active substance sodium lauryl ether sulfate | 31.6 mN/m |
| Texapon ® NSO with tartaric acid | 5% by weight active substance sodium lauryl ether sulfate 0.5% by weight tartaric acid | 30.03 mN/m |

Determination of Foaming Behavior

To determine foaming behavior, the foaming kinetics after 30 seconds and the foam potential after 60 s and 180 s were measured by the rotor foam method (DIN 13996 in preparation). The rotor foam tester consists of a heatable, double-walled cylindrical glass vessel with an internal diameter of 17.5 cm. A scale in mm is provided on the cylindrical glass vessel for reading off the foam height and the liquid level. In addition, the glass vessel is provided with a Styropor lid which is used both to cover and to insulate the vessel. The stirrer consists of a special stirring head with a stirrer shaft 28 cm in length and 1 cm in diameter and a JK stirrer with a digital revolution counter. A thermostat, a stopwatch and a thermometer (digital) are also required.

The test solution was prepared with water of a certain hardness (15° dH). 200 ml of the sample preheated to 30±1° C. were slowly poured in at the rim of the glass vessel which was covered with the Styropor lid when the required temperature of 30±1° C. had been reached. The rotor speed was 1300 r.p.m.

The first foam height value was determined after 30 seconds. To this end, the stirrer was switched off for at most 10 seconds. The foam volume was then determined after 60 and 180 seconds.

TABLE 1b

Foam behavior of the surfactant solution containing tartaric acid and the pure surfactant solution

| Substance | Concentration | | Foam behavior |
|---|---|---|---|
| Texapon ® NSO | 0.1% by weight active substance sodium lauryl ether sulfate | 30 s 60 s 180 s | 10.8 cm 11.0 cm 11.0 cm |
| Texapon ® NSO with tartaric acid | 0.1% by weight active substance sodium lauryl ether sulfate 0.01% by weight tartaric acid | 30 s 60 s 180 s | 10.8 cn 11.0 cm 11.0 cm |
| Texapon ® NSO with laureth-4-citrate | 0.1% by weight active substance sodium lauryl ether sulfate 0.01% by weight laureth-4-citrate | 30 s 60 s 180 s | 9.5 cm 10.8 cm 11.0 cm |

It is clear from the test results (Tables 1a and 1b) that the addition of tartaric acid or lareth-4-citrate does not significantly affect the surface activity or the foam behavior of the anionic surfactant so that it may be assumed that the addition of tartaric acid or laureth-4-citrate does not reduce the detersive performance of the surfactant although the irritation potential is reduced.

Determination of the Irritation Potential—In Vitro Test: HET-CAM Test, Reaction Time Method The irritation potential was determined by a HET-CAM test as described in "Der HET-CAM-Test", Euro Cosmetics 11/12-99, pp. 29-33, Dunja et al.

TABLE 2

Reaction time method and end point evaluation by the HET-CAM test

| Substance | Concentration | Reaction time [Q value] |
|---|---|---|
| Texapon ® ASV | 5% by weight active substance mixture of special mild fatty alcohol ether sulfates | 1.00 |
| Texapon ® NSO | 5% by weight active substance sodium lauryl ether sulfate | 1.63 |
| Texapon ® NSO | 3% by weight active substance sodium lauryl ether sulfate 0.5% by weight tartaric acid | 1.47 |
| Texapon ® NSO with tartaric acid | 5% by weight active substance sodium lauryl ether sulfate 0.5% by weight tartaric acid | 1.01 |
| Texapon ® NSO with laureth-4-citrate | 3.75% by weight active substance sodium lauryl ether sulfate 1.25% by weight laureth-4-citrate | 0.95 |

The results (Table 2) show a distinct reduction in the irritation potential of anionic surfactants by the addition of tartaric acid or laureth-4-citrate. The reaction time [Q value] is reduced to 62% of the original value by the addition of 10% by weight tartaric acid (based on the quantity of anionic surfactants) and to as low as 58% of the original value by the addition of 33% laureth-4-citrate (based on the quantity of anionic surfactants).

The invention claimed is:

1. A process for improving the compatibility of a composition comprising anionic surfactants with skin, mucous membrane and tissue, which comprises: incorporating a compatibility improving amount of an ethoxylated alcohol ester of a hydroxycarboxylic acid of formula:

$$R^3O-(EO)_x-Z \quad (III)$$

wherein, $R^3$ is an alkyl group containing 6 to 22 carbon atoms, (EO) is an ethoxy group, x is an integer of 1 to 10, and Z is a hydroxycarboxylic acid residue, into the composition comprising the anionic surtactant, whereby, the compatibility of the composition comprising the anionic surfactant is improved when compared to a composition which does not contain the ethoxylated alcohol ester of the hydroxycarboxylic acid.

2. The process of claim 1, wherein, 25 to 50% by weight, based on a quantity of anionic surfactants, of esters of α-hydroxycarboxylic acids with ethoxylated alcohols are incorporated into the composition.

3. The process of claim 1, wherein, the composition comprising anionic surfactants further comprises at least one member selected from the group consisting of other mild surfactants, emulsifiers, lipid layer enhancers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and further auxiliaries and additives.

4. The process of claim 1 wherein $R^3$ contains from 12 to 14 carbon atoms.

5. The process of claim 1 wherein x is an Integer of from 2 to 10.

6. The process of claim 1 wherein, Z comprises a residue of at least one acid selected from the group consisting of tartaric acid, mandelic acid, lactic acid, malic acid and citric acid.

7. The process of claim 1, wherein, Z is a residue of an α-hydroxycarboxylic acid.

8. A composition comprising: an anionic surfactant and 25% to 50% by weight, based on weight of the anionic surfactant, of an ethoxylated alcohol ester of a hydroxycarboxylic acid of formula:

$$R^3O-(EO)_x-Z \quad (III)$$

wherein. $R^3$ is an alkyl group containing 6 to 22 carbon atoms. (EO) is an ethoxy group. X is an integer from 1 to 10, and Z is a hydroxycarboxylic acid residue.

9. The composition of claim 8, wherein, x is an integer of from 2 to 10.

10. The composition of claim 8 further comprising at least one member selected from the group consisting of other mild surfactants, emulsifiers, lipid layer enhancers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the-like-as further auxiliaries and additives.

11. The composition of claim 8, wherein, the composition has a surface activity of at least 20 mN/in (as measured at 21±1° C. by DIN 53914 method) and a Q value of less than 75% in the HET-CAM Test based on a surfactant solution comprising the anionic surfactant without the ethoxylated alcohol ester of the hydroxycarboxylic acid.

12. The composition of claim 8, wherein, the hydroxycarboxylic acid residue comprises at least one residue of an acid selected from the group consisting of tartaric acid, mandelic acid, lactic acid, malic acid and citric acid.

13. The composition of claim 8, wherein, the ester of the hydroxycarboxylic acid comprises an ester of an α-hydroxycarboxylic acid.

* * * * *